United States Patent [19]

Magnussen, Jr.

[11] Patent Number: 5,062,706
[45] Date of Patent: Nov. 5, 1991

[54] HIGH PRESSURE FLUID SAMPLE FLOW CELL WITH CIRCUMFERENTIAL WINDOW EDGE SEAL

[75] Inventor: Haakon T. Magnussen, Jr., Orinda, Calif.

[73] Assignee: Rainin Instrument Co., Inc., Emeryville, Calif.

[21] Appl. No.: 510,038

[22] Filed: Apr. 16, 1990

[51] Int. Cl.[5] .................................................. G02B 7/00
[52] U.S. Cl. ...................................... 356/246; 359/894
[58] Field of Search .......................... 356/246; 350/319

[56] References Cited

U.S. PATENT DOCUMENTS

| | | | |
|---|---|---|---|
| 2,857,803 | 10/1958 | Reinecke et al. | 356/246 |
| 3,625,390 | 12/1971 | Meginnis | 350/319 |
| 3,746,431 | 7/1973 | Meginnis | 350/319 |
| 3,951,301 | 4/1976 | Meginnis | 350/319 |
| 4,838,688 | 6/1989 | Rhoads | 356/246 |

OTHER PUBLICATIONS

Abdullah et al., "Variable Temperature High-Pressure Raman Cell", *J. Phys. E: Science Instrum.*, vol. 13, No. 11 (Nov. 1980).

*Primary Examiner*—Richard A. Rosenberger
*Attorney, Agent, or Firm*—Robert R. Meads

[57] ABSTRACT

A fluid sample flow cell including a high pressure fluid tight circumferential edge seal for a window in the body of the flow cell.

7 Claims, 2 Drawing Sheets

HIGH PRESSURE FLUID SAMPLE FLOW CELL WITH CIRCUMFERENTIAL WINDOW EDGE SEAL

BACKGROUND

The present invention relates to improvements in fluid sample flow cells and more particularly to a high pressure fluid sample flow cell with a circumferential window edge seal.

Fluid sample flow cells commonly comprise a metal or plastic cell body having a fluid passageway therethrough. A fluid inlet connected to one end of the passageway flows a sample fluid with analytes to be detected from a sample source, such as an LC column. The sample fluid flows along the passageway to exit at an outlet from an opposite end of the passageway. While the fluid is flowing along the passageway, it is exposed to a light beam transmitted from a light source to a light detector through windows at opposite ends or sides of the passageway. Variations in light absorbance monitored at the detector are utilized to identify and quantify the analytes in the fluid sample.

In such flow cells it is of course important that fluid not leak from the cell body and that the connections between the windows and the cell body be fluid tight. In the past, such fluid tight seals have been defined by window face sealing means such as annular plastic gasket or O-ring seals. To create a window face seal the annular seal has been placed on a flat face of the window and the window and seal forced tightly together as by clamps, clips and the like. U.S. Pat. Nos. 3,515,491; 3,647,304 and 4,374,620 describe such window face seals.

In high pressure flow systems having an internal fluid pressure of 1000 psi and more, the challenges relative to fluid tight seals are much more severe than in low pressure systems. Yet today, window seals in such high pressure systems still utilize the standard face seal approach only with greater and greater forces being developed between the annular seals and the face surfaces of the windows. In practice, this has resulted in undesired fracturing and cracking of cell windows and rapid deterioration of over-stressed seals.

SUMMARY OF INVENTION

The present invention overcomes the foregoing problems and limitations associated with standard window face seals in fluid sample cells by providing a high pressure circumferential window edge seal. The sealing forces exerted on the window in such a sealing configuration are radial along lines of greatest strength of the window and hence do not produce undesired window fractures or seal deteriorations even when sealing against flow cell internal fluid pressures in excess of 10,000 psi.

DETAILED DESCRIPTION OF PREFERRED EMBODIMENTS OF INVENTION

Figure 1:
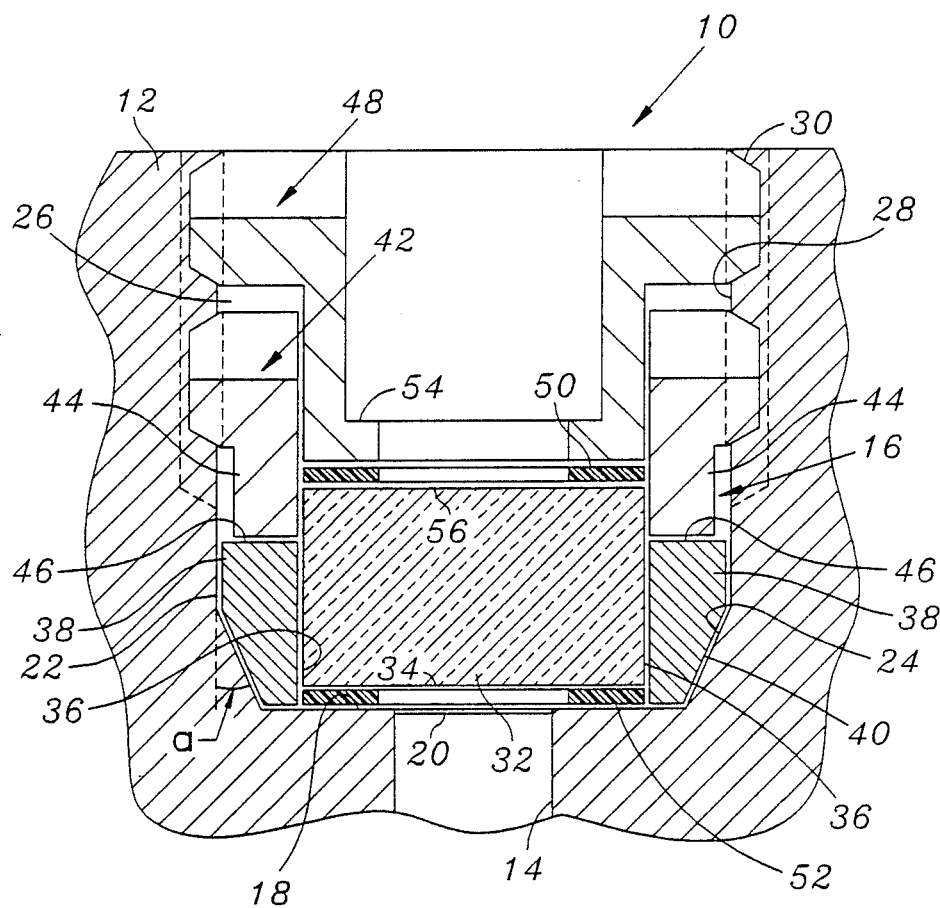
FIG. 1 is a cross-sectional view of a portion of a fluid sample flow cell including a metal cell body and circumferential window edge seal in accordance with the present invention.

In FIG. 1, the fluid sample flow cell is represented by the number 10 and comprises a chemically inert metal cell body 12 having a passageway 14 therethrough.

Connecting to the passageway 14 is a window receiving cavity 16. The cavity 16 includes (i) a flat inner end 18 surrounding an opening 20 to the passageway 14, (ii) an inner end portion 22 including an inner axially extending annular surface 24 diverging radially outwardly at an angle a, and (iii) an outer end portion 26 including an axially extending internally threaded annular surface 28 adjacent an outer end 30 of the cavity.

Seated in the inner end portion 22 of the cavity 16 is a cylindrical window 32. The window may be formed of quartz and includes a flat end face 34 over the flat inner end 18 of the cavity and a cylindrical circumferential edge 36 adjacent the inner annular surface 24 of the cavity.

Seated around the circumferential edge 36 of the window 32 and adjacent the inner annular surface of the cavity is an annular slightly deformable ferrule 38. The ferrule 38 preferably is formed from a chemically inert plastic and includes an axially extending outer surface 40 diverging radially outwardly at the angle a for mating with the outwardly diverging annular surface 24 of the cavity.

In order to create the desired circumferential window edge seal, a metal ferrule clamp 42 comprising a tubular screw is threaded into the outer end portion 26 of the cavity with an annular end 44 of the clamp pressing axially on an outer end 46 of the ferrule 38. As the ferrule clamp 42 is tightened in the cavity 16, the annular end 44 exerts a sufficient force on the ferrule as to wedge it tightly between the circumferential edge 36 of the window 32 and the annular surface 24 of the cavity creating an high pressure fluid tight seal therebetween which in practice withstands fluid pressures in excess of 10,000 psi in the flow cell 10. In creating such a high pressure seal, the ferrule 38 is acting on the circumferential edge 36 of the window 32 and exerting radial forces along the lines of maximum strength of the window. Thus, in creating the desired high pressure fluid tight seal, the present invention neither fractures the window nor over-stresses a fragile annular seal.

To complete the preferred embodiment of the present invention, the illustrated flow cell includes a window clamp 48 and plastic annular window pads 50 and 52. The window clamp 48 comprises a tubular metal screw threaded into the outer end portion 26 of the cavity 16 with an inner annular end 54 pressing axially on the annular window pad 50 to compress it slightly and create a restraining force against an outer end portion 56 of the window 32 and a cushion for the window. The window pad 52 is positioned around the opening 20 between the flat inner end 18 of the cavity and the flat end 34 of the window to provide a cushion for the window on the end of the cavity.

As previously stated, the flow cell illustrated in FIG. 1 preferably includes a metal cell body and is designed to handle internal fluid pressures in excess of 10,000 psi. For such a flow cell, the following dimensional relationships may apply:

passageway 14: internal diameter, 0.5–3 mm window 32: outer diameter, 1-6 mm thickness, approximately 3 mm ferrule 38: internal diameter, 1-6 mm thickness, slightly less than 3 mm angle a: 15°-45°

Figure 2:
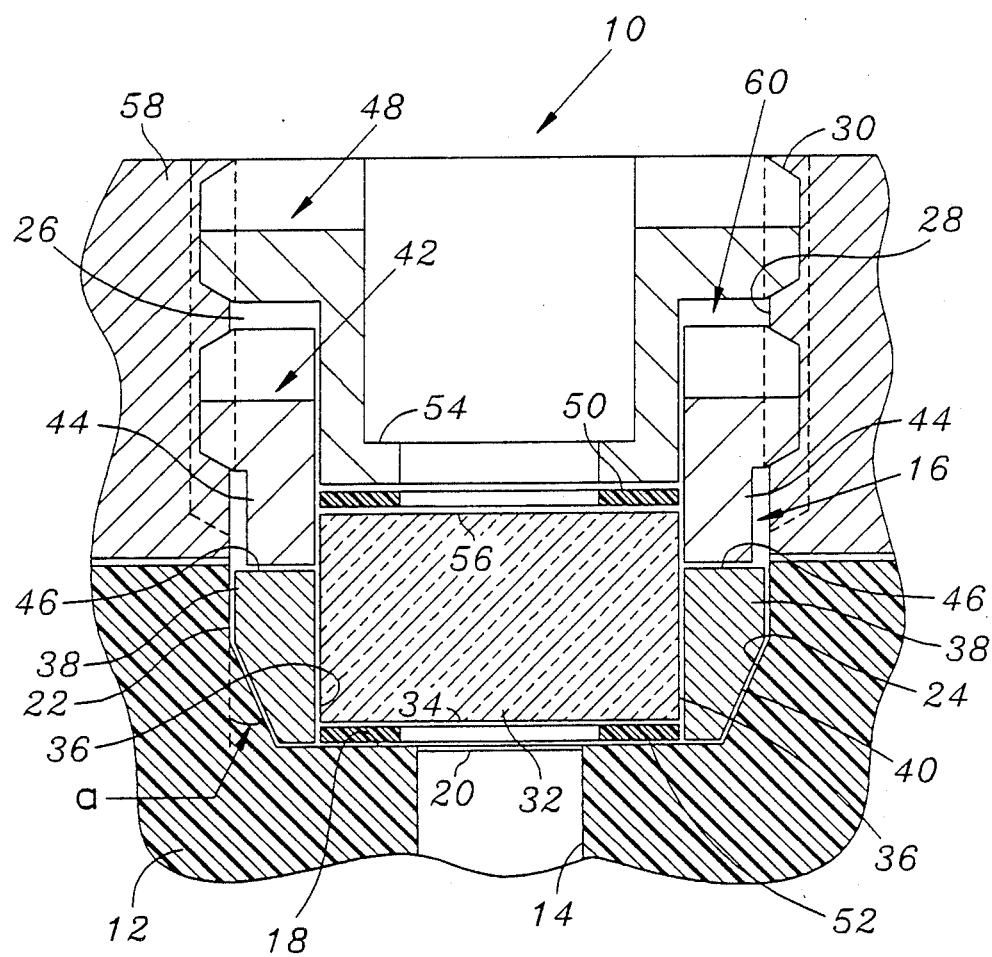
FIG. 2 is a cross-sectional view of a portion of a fluid sample flow cell including a plastic cell body and circumferential window edge seal in accordance with the present invention.

A similar flow cell comprising a plastic inner cell body 12 with circumferential window edge seal is illustrated in FIG. 2 and is designed to handle internal fluid pressures between 5,000 and 6,000 psi. Elements of the flow cell shown in FIG. 2 corresponding to elements of the flow cell of FIG. 1 bear the same reference numbers and their description will not be repeated. However, as represented in FIG. 2, the plastic inner cell body 12 including the passageway 14 is surrounded and supported by conventional means in an outer metal housing 58. The window receiving cavity 16 includes and is aligned with a side opening 60 in the housing 58. In this regard, the lower end of the cavity 16 includes the flat end face 18 and annular surface 24 while the opening 60 includes the internally threaded surface for receiving the tubular screws comprising the ferrule and window clamps 42 and 48. The function of the ferrule 38 is the same in creating a high pressure fluid tight circumferential edge seal on the window 32.

While particular forms of the present invention have been described in detail hereinabove, such description is by way of example only. Changes and modifications may be made in the illustrated embodiments without departing from the spirit or scope of the present invention as defined by the following claims.

I claim:

1. In a high pressure flow cell including a cell body having a passageway therethrough and windows for passing light through fluid flowing in the passageway, a high pressure circumferential window edge seal, comprising:

a window receiving cavity including a flat inner end surrounding an opening to the fluid passageway, an inner end portion including an inner axially extending radially outwardly diverging annular surface adjacent the inner end, and a outer end portion including an axially extending internally threaded annular surface adjacent an outer end of the cavity;

a cylindrical window in the inner end portion of the cavity and including a flat end over the flat inner end of the cavity and a cylindrical circumferential edge adjacent the inner annular surface of the cavity;

an annular ferrule around the circumferential edge of the window and adjacent the inner annular surface of the cavity, the ferrule including an axially extending radially outwardly diverging surface for mating with the outwardly diverging surface of the inner annular end portion of the cavity; and a ferrule clamp comprising a tubular screw threaded into the outer end portion of the cavity and including and annular end for pressing axially on an outer end of the ferrule to wedge the ferrule and create a fluid tight high pressure seal between the circumferential edge of the window and the inner annular surface of the cavity.

2. The combination of claim 1 further including a window clamp comprising a tubular screw threaded into the outer end portion of the cavity and including an annular end for pressing axially on an outer end portion of the window.

3. The combination of claim 2 further including an annular window pad between the annular end of the window clamp and the outer end portion of the window.

4. The combination of claim 3 further including an annular window pad between the flat inner end of the cavity surrounding the opening to the passageway and flat end of the window 5. The combination of claim 1 wherein the window receiving cavity is in a metal cell body.

6. The combination of claim 1 wherein the flat inner end and inner end portion of the window receiving cavity are in a plastic inner cell body and the outer end portion of the window receiving cavity is in an outer metal housing surrounding and supporting the inner plastic cell body.

7. In a high pressure flow cell including a cell body having a passageway therethrough and windows for passing light through fluid flowing in the passageway, a high pressure circumferential window edge seal, comprising:

a window receiving cavity including an inner end surrounding an opening to a fluid passageway, an inner end portion including an inner axially extending radially outwardly diverging annular surface adjacent the inner end;

a cylindrical window in the inner end portion of the cavity and including an end over the inner end of the cavity and a cylindrical circumferential edge adjacent the inner annular surface of the cavity;

an annular ferrule around the circumferential edge of the window and adjacent the inner annular surface of the cavity, the ferrule including an axially extending radially outwardly diverging surface for mating with the outwardly diverging surface of the inner annular end portion of the cavity; and means for wedging the ferrule between the circumferential edge of the window and the inner annular surface of the cavity to create a fluid tight high pressure seal therebetween.

* * * * *